United States Patent [19]

Alcond

[11] Patent Number: 4,674,506
[45] Date of Patent: Jun. 23, 1987

[54] SURGICAL ANASTOMOSIS STENT

[76] Inventor: Kirk Alcond, 183 Monte Vista, Unit D, Costa Mesa, Calif. 92627

[21] Appl. No.: 676,245

[22] Filed: Nov. 29, 1984

[51] Int. Cl.$^4$ .............................................. A61B 17/11
[52] U.S. Cl. .................................. 128/334 R; 623/12; 623/66; 128/1 R
[58] Field of Search ............... 128/334 R, 334 C, 1 R; 623/11, 12

[56] References Cited

U.S. PATENT DOCUMENTS

| | | | |
|---|---|---|---|
| 3,304,557 | 2/1967 | Polansky | 128/1 R X |
| 3,515,124 | 6/1970 | Gurchot | 128/1 R |
| 3,620,218 | 11/1971 | Schmitt et al. | 128/334 R |
| 3,990,434 | 11/1976 | Free | 128/1 R |
| 4,061,134 | 12/1977 | Samuels et al. | 128/1 R |

Primary Examiner—Richard J. Apley
Assistant Examiner—Alan W. Cannon
Attorney, Agent, or Firm—Fay, Sharpe, Beall, Fagan, Minnich & McKee

[57] ABSTRACT

A surgical stent (10) having elongate opposite end portions (12, 14) of different cross-sectional dimensions terminating in rounded terminal elements (16, 18) with rounded exterior surfaces is disclosed together with a surgical procedure for anastomosis of anatomical tubular organ structures. The stent contains a central canal (24) providing passage through the entire length of the stent and a plurality of annular ribs (20, 22) surrounding the exterior surfaces of the elongate portions (12, 14). The different cross-sectional dimensions of the two elongate portions (12, 14) allows selection of a stent to conform with the interior diameters of the lumena of the two sections of the tubular organ structure to be joined. The rounded exterior surfaces of the terminal elements (16, 18) and annular ribs (20, 22) assures a minimization of surgical trauma to the organ structure while the ribs minimize post-operative leakage at the site of the reanastomized tubular organ structure end sections.

27 Claims, 11 Drawing Figures

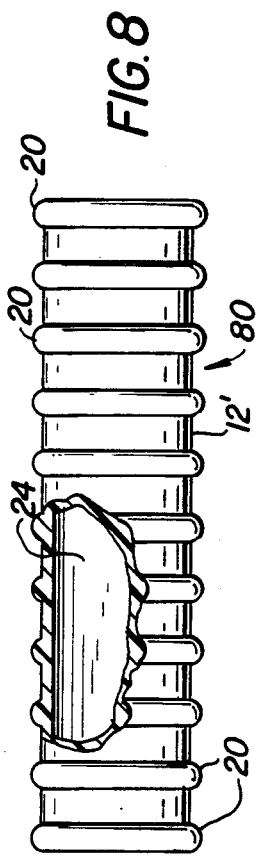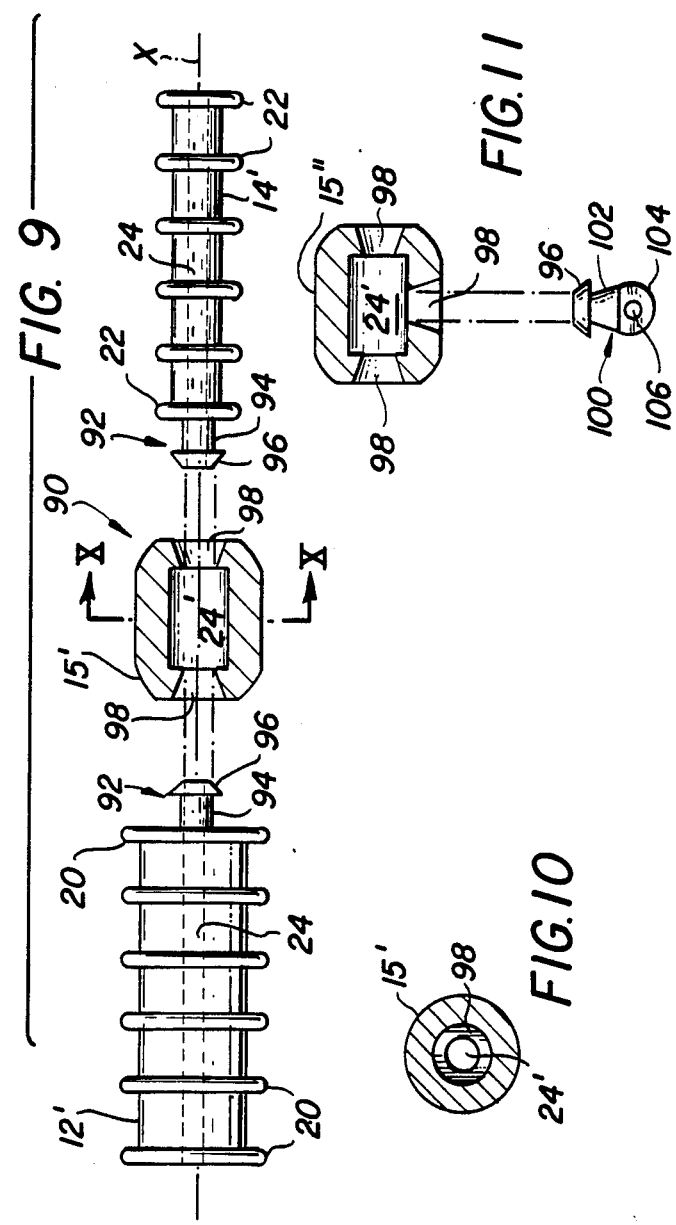

SURGICAL ANASTOMOSIS STENT

TECHNICAL FIELD

This invention pertains to surgical couplings and, more particularly, to devices and surgical procedures for affecting anastomosis of tubular organ structures.

During recent years there has been an increasing demand for surgical anastomosis of anatomical tubular organ structures such as the urethra/ureter, bowel, vas deferens, trachea, and esophagus. When thin-walled channels such as those of the bowel are anastomized, it is common practice to cut their ends obliquely, thereby increasing the circumference of the anastomose and reducing chances of stricture. With thick-walled structures such as the vas deferens however, the lumen of one side of the structure (e.g., the testicular side of the vas deferens) post-operatively dilates, causing a thinning of the wall thickness without appreciable change in exterior diameter. Consequently, oblique cuts between the dialated and undialated sides of a thick-walled organ structure result in unsatisfactory angulation.

There are currently three main surgical procedures in use for anastomosis of thick-walled tubular structures such as the vas deferens. In the first of these procedures, macro surgery, an incision is made through the wall of the anatomical cavity (e.g., the upper anterior wall of the scrotum if the procedure is for a vasectomy) containing the tubular structure. The tubular structure is then resectioned by removing scarred tissue at both ends of the tubular structure, and a removable stent formed by a sharp-ended needle or wire is inserted into the lumen at the resectioned end of one of the tubular organ structures to be rejoined. The point of the stent is then forced through the wall of the organ structure and positioned so that the opposite end of the stent protrudes sufficiently to receive the lumen of the resectioned other side of the structure. In effect, the stent serves to assure accurate tubal re-approximation by aligning the lumen of the severed organ structures in a position suitable for suturing. Immediately after suturing, the needle is pulled through the wall thickness and removed.

This method has proved unsatisfactory in many cases because of the frequency of stricture, which ultimately results in blockage occuring at the site of the union. Also, the absence of support during tissue joinder leaves the union susceptible to accidents and strains. In one improvement upon this procedure, the stent was left in place during healing. This however, required the incision into the interior anatomical cavity containing the severed tubular structure to be left open until the union had healed and the stent could be removed.

In a further refinement of this procedure, a long flexible stent (10 inches or longer of monofilament nylon or plastic tubing with needles attached to both ends), is inserted into the lumen and through the wall thicknesses of each of the severed tubular segments. After anastomosis, the needles are removed from the stent and the ends of the stent are positioned on the outside of the incision into the cavity. Later, after healing of the tubular structure, one end of the stent is pulled, thereby drawing the entire stent from the organ structure and through the incision.

Although this refinement is a procedure still in common use because of its low cost-benefit ratio, it is accompanied by particularly undesirable aspects. First, the refinement traumatizes the lumen, adjoining muscle and connective tissue layers at two sites. Commonly, a 0.037 inch diameter stent of Silastic tubing is pushed through a lumen having an interior diameter as small as 0.025 inches and outwardly through a tissue wall thickness of about 0.040 inches. Second, the passage of the stent through the cavity incision serves as a track for the entrance of infection. Moreover, evidence exists which shows that obstructions occur at sites where the stent exits through the walls of the vas deferens.

In the second procedure, macrosurgery using an absorbable inter-luminal stent, short solid stents of absorbable material such as chromic catgut or Dexon (e.g., a polygylcolic acid, synthetic, absorbable suture), are inserted into the lumen and used to align the opposite sections for suturing. After suturing, these stents are left in place until they dissolve by liquifaction. This procedure has proven to be less damaging to the delicate lumen and muscular wall tissue than previous methods (follow-up studies have shown that there is no discernable residual stent material and no reaction to the stent material at six months), primarily because this procedure eliminates the necessity of puncturing the muscle and connective tissue layers forming the tubal walls. This procedure does suffer however, from the risk of gaps occurring in either the anastomoses or suture punctures through the walls, which can subsequently lead to leakage of effluent (e.g., sperm) causing granuloma and a resultant stricture of the lumen.

In the third procedure, microsurgery, no stent is used. Here, microsurgical techniques are used at a magnification of up to forty times. Clean, unobstructed ends of the organ structure to be reunited are gently clamped side by side. A series of micro-sutures is placed in the luminal mucosa, drawn and tied. This draws the two sections of the organ structure together and accurately aligns the lumen. Then, a second series of sutures is placed in the muscular tissue around the periphery of the organ structure to complete the anastomosis.

Due to dilation of the lumen, the interior lumen diameter may increase by as much as 70%. With the vas deferens, dialation appears to be due to increased internal pressure from accumulation of spermatic fluid in the testicular segment. A mismatch can easily occur during reanastomosis due to the differences in luminal diameters of the testicular and urethal segments of the vas and cause obstruction of the lumen. Although microsurgical techniques make careful approximation of these mucosal lumina possible, exceptionally advanced skill is required on the part of the surgeon. Moreover, because no internal stent is present to preserve the lumen, tissue regeneration at the site can cause partial or complete occlusion. Although this procedure is not suitable for the "occasional microsurgeon," when performed by a skilled surgeon it is both expensive and time consuming, requiring several hours for reanastomosis of the vas deferens for example.

STATEMENT OF THE INVENTION

Accordingly, it is an object of this invention to provide an improved process and device for the anastomosis of tubular organ structures.

It is another object to provide a process and a device for more reliably performing an anastomosis of tubular organ structures.

It is yet another object to provide a process and a device for minimizing the creation of sites for the occurrence of infection after anastomosis of a tubular organ structure.

It is still another object to provide a process and a device for minimizing the occurrence of granduloma formation at the site of a tubular anastomosis.

It is still yet another object to provide a process and a device for preserving intraluminal passage between severed tubular sections during an anastomosis.

It is a further object to provide a process and a device for enabling more accurate luminal approximation during anastomosis.

It is also an object to provide a process and a device for enabling reliable anastomosis of severed tubular structures having different internal diameters.

These and other objects are attained with a process and a stent for surgically coupling the end sections of a severed anatomical tubular organ structure. The stent has elongate portions with cross-sectional dimensions conforming to the internal lumen diameters of the severed end sections. The elongate portions terminate in rounded terminal elements and a central canal extends between the rounded elements and the elongate portions. In the process, both ends of the severed tubular organ structure are resectioned, their internal diameters are measured and a stent having portions with external cross-sectional dimensions conforming to the measured diameters is selected. The elongate portions of the selected stent are inserted into the lumen of the resectioned ends and the resectioned ends are drawn together over the stent.

BRIEF DESCRIPTION OF THE DRAWINGS

A more complete appreciation of this invention, and many of the attendant advantages thereof, will be readily apparent as the same becomes better understood by reference to the following detailed description when considered in conjunction with the accompanying drawings in which like reference symbols indicate the same or similar components, wherein:

FIG. 8 shows a partially cutaway plan view of another embodiment of the present invention;

FIG. 9 shows an exploded plan view of an embodiment having a central element shown in cross-sectional detail;

FIG. 10 shows a cross-sectional view taken along line X—X in FIG. 9; and

FIG. 11 shows an exploded plan view of part of an alternative embodiment of the assembly shown in FIG. 9.

DETAILED DESCRIPTION OF THE INVENTION

Figure 1:
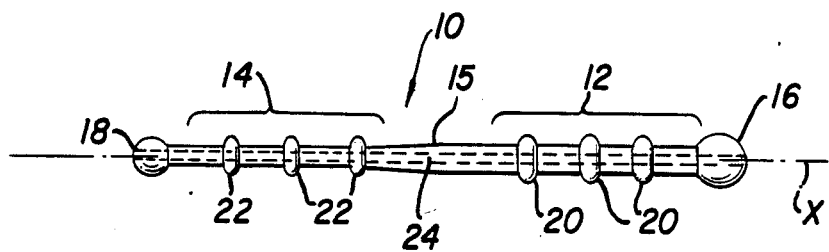
FIG. 1 is an enlarged plan view of a surgical stent constructed in accordance with the principles of the present invention.

Refer now to the drawings and, in particular, to FIG. 1 where a stent 10 constructed according to the principles of the present invention is shown. Stent 10 has a first elongate portion 12 characterized by a greater cross-sectional diameter and a second elongate portion 14 characterized by a lesser cross-sectional diameter, joined by an intermediate portion 15 which provides a smooth transition between the different exterior diameters of portions 12, 14. Typically, portions 12 and 14 are circular in shape. Rounded terminal elements 16, 18 respectively terminate the distal ends of first and second portions 12, 14. A plurality of annular ribs 20, 22 having rounded exterior surfaces are respectively disposed around the exterior circumferential surfaces of first portion 12 and second portion 14. The cross-sectional diameter of rounded terminal elements 16, 18 transverse to the longitudinal axis X of stent 10 are greater than the exterior cross-sectional diameters of the adjoining first and second portions 12, 14, respectively; however, the transverse cross-sectional diameter of element 16 is greater than that of element 18. A central canal 24 extends along the axial length of stent 10, through first and second portions 12, 14 and opens at the distal extremeties of rounded terminal elements 16, 18. Although the exterior cross sectional dimensions of the first and second portions of stent 10 and their associated rounded end elements 16, 18 and ribs 20, 22 are different with element 16 and ribs 20 forming part of the exterior of first portion 12 having greater cross-sectional dimensions than element 18 and ribs 22 forming part of second portion 14, the interior diameter of canal 24 is substantially constant throughout the length of stent 10.

Stent 10 is formed from a tissue absorbable material such as Dexon (i.e., polyglycolic acid synthetic absorbable material), and is quite flexible. The length and cross-sectional dimensions of stent 10 are determined primarily by the ranges of interior diameters of the particular anatomical tubular organ structure to be recanalized. For a vas deferens, for example, stent 10 may be reasonably manufactured in twelve different sizes. These sizes would range from a minimum of approximately 0.6 millimeters at the urethral (second portion 14) and 1.3 millimeters at the testicular (first portion 12) end, to a maximum of approximately 1.3 millimeters at the urethral end and 2.0 millimeters at the testicular end. The rounded exterior surfaces of ribs 20, 22 and rounded terminal elements 16, 18 eliminate the occurrence of sharp angles and edges between stent 10 and the interior tissues of any anatomical lumen into which stent 10 is inserted, thereby minimizing trauma to the lumen tissue and hastening patient recovery. Moreover, the difference in transverse cross-sectional dimensions between rounded terminal element 16, 18, annular ribs 20, 22 and the intermediate underlying first and second portions 12, 14 of stent 10 eliminates slippage of either section of a recanalized organ structure relative to stent 10 while minimizing leakage between the ends of the recanalized organ structure of effluent passing through the reunited lumen of that structure. After healing of the reunited organ structure, stent 10 dissolves and leaves a functional tubular organ structure with an accurately approximated, open lumen.

Figure 2:
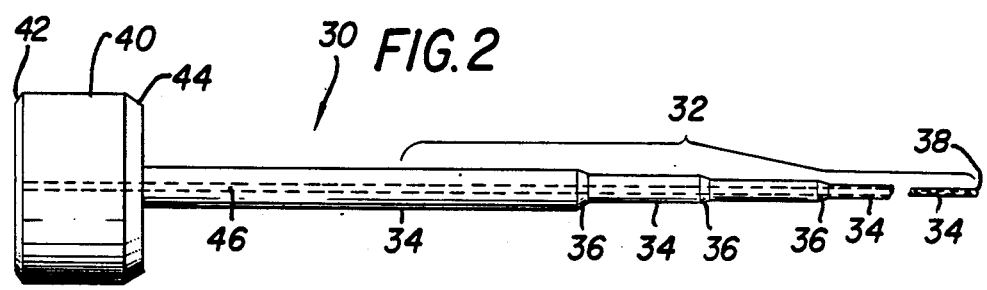
FIG. 2 shows an enlarged plan view of a combination syringe tip and gauge for use in the process of the present invention.

Applicator tip 30, shown greatly enlarged in FIG. 2, is particularly suitable for use during anastomosis according to principles of the present invention. Applicator tip 30 includes a measuring rod 32 formed by a plurality of sections 34 of different, constant diameters joined together by intermediate beveled edges 36 in a continuous stepped sequence. The tip 38 at the distal end of the smallest of the sections 34 is rounded to avoid the occurrence of edges or angles which may possibly traumatize the tissue of a lumen. The proximal end of applicator tip 30 is formed by an enlarged annular portion 40 having beveled rims 42, 44. An open lumen 46 extends completely through applicator tip 30, thereby allowing passage of an effluent such as a saline solution or an anesthetic between the proximal end of annular portion 40 and distal rounded tip 38. Preferably, applicator tip 30 is made from a surgical grade of stainless steel, although it may also be made as a disposable item constructed from a less expensive material such as Teflon.

Tip 30 is designed to serve as the distal portion of a surgical syringe. In such an application, annular portion 40 is held and forms a plug at the distal end of the syringe reservoir, while effluent from the syringe reservoir is ejected through measuring rod 32 via lumen 46. The adjoining, stepped sections 34 forming measuring rod 32 enable the syringe to obtain accurate measurements of the internal diameters of resectioned segments of a tubular organ structure simply by insertion of measuring rod 32 into a lumen until the lumen begins to resist further insertion. The particular section 34 encountering such resistance provides an immediate indication of the lumen's internal diameter.

The several advantages provided by the present invention are best illustrated by reference to an exemplary surgical procedure. Stent 10 is particularly suitable for joining small anatomical tubes such as the vas deferens. Reanastomosis of a vas deferens (i.e., a vasovasotomy) is one such illustrative procedure. In vasectomy, the scrotum of the patient is injected with a local anesthetic. The area is then shaved, disinfected and stretched over the surgeon's fingers for visual examination and a small, approximately one-quarter inch, incision is made in the upper anterior portion of the scrotum. In a vasectomy, the vas deferens is typically folded and then tied with suture material. The knuckle of the tied vas is then severed and the vas is placed back inside the scrotum with the suture holding the severed ends in a side-by-side configuration. After vasectomy, fibrosis forms around the suture and sperm granduloma formation may occur at the end of the severed urethal segment.

Figure 3:
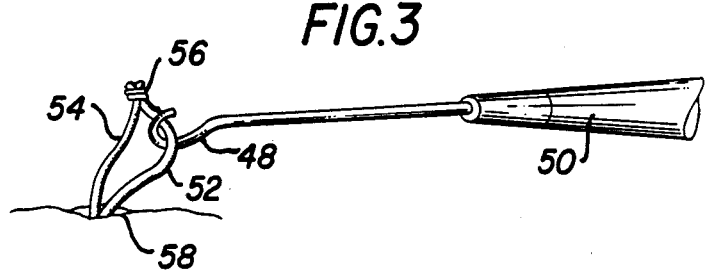
FIG. 3 shows one step during the anastomosis of a anatomical tubular organ structure.

In a vasovasotomy, the scrotal region is injected with a local anesthetic. The scrotum is then shaved, disinfected and stretched across the surgeon's fingers to be visually examined to determine the location of surface blood vessels. A small, approximately one-quarter inch incision is made in the upper anterior portion of the scrotum with particular care to avoid severing blood vessels. A hook 48 of a surgical probe 50, shown in FIG. 3, is inserted through the incision to engage one limb 52 of a severed vas which is frequently still joined to the other limb 54 by the surgical suture 56 applied during the vasectomy. Once the vas is located, it is pulled through the incision 58 by hook 48. The severed end sections are located and the suture, fibrosis and any granduloma formation are removed by resectioning both the testicular 52 and urethal 54 limbs of the vas, usually by snipping off the damaged tissue at the end portions of both limbs.

Figure 4:
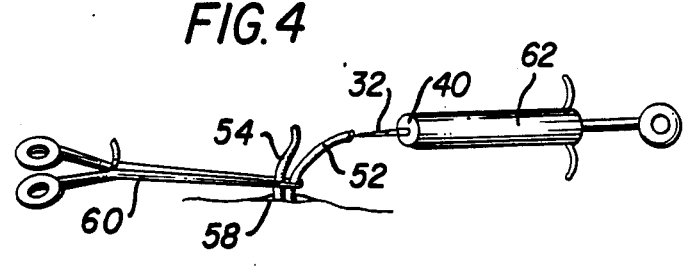
FIG. 4 shows a second step during anastomosis of an anatomical tubular organ structure.

As shown in FIG. 4, after resectioning, both ends 52, 54 of the vas are gently held by self-locking forceps 60 while the lumina of both ends 52, 54 are irrigated with a saline solution administered by a standard, self-filling water syringe 62 bearing annular portion 40 and measuring rod 32 of the applicator tip 30 shown in FIG. 2. During the irrigation process, measuring rod 32 is gently inserted into the lumina of limbs 52, 54 to obtain accurate measurements of their internal diameters. The saline solution irrigation assists in removing adhesions and debris from the lumen's interior.

Figure 5:
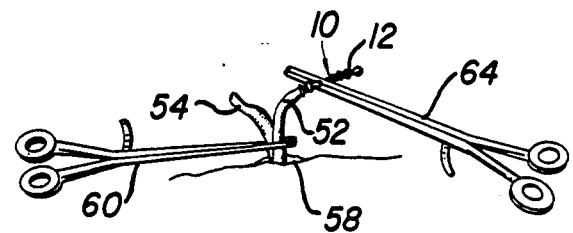
FIG. 5 shows a further step during the process of anastomosis of an anatomical tubular organ structure.
Figure 6:
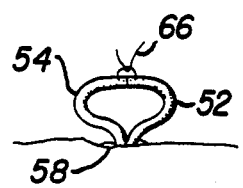
FIG. 6 shows a subsequent step during anastomosis of an anatomical tubular organ structure.

Using the measurements obtained for the lumina, a stent 10 is selected with a greater cross-sectional portion 12 conforming to the measured interior diameter of testicular limb 52 and a lesser cross-sectional diameter portion 14 conforming to the measured interior diameter of urethal limb 54. As shown in FIG. 5, a selected stent with first and second portions conforming to the measured interior lumina diameters is held across its center portion by a second pair of self-locking forceps 64 while greater cross-sectional portion 12 is inserted into the resectioned testicular end 52 of the vas. Lesser cross-sectional portion 14 is subsequently inserted into resectioned urethal end 54. Alternatively, the sequence of insertions may, in the discretion of the surgeon, be reversed with the lesser diameter portion 14 being inserted first into resectioned urethal end 54. Then, as shown in FIG. 6, a single suture 66, preferably of a tissue absorbable material, is drawn through the mucosa of both sides of the resectioned ends, thereby drawing the testicular and urethal ends 52, 54 together over the central section of stent 10.

Figure 7:
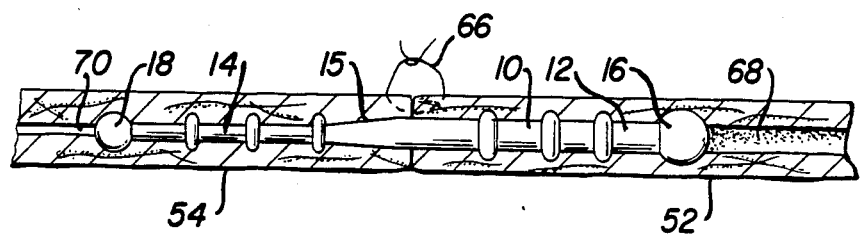
FIG. 7 provides a partially cutaway view of both ends of an anatomical tubular organ structure coupled with the stent shown in FIG. 1 according to the principles of the present invention.

It is noted that, as shown in FIG. 7, suture 66 passes through the muscle tissue of both end sections, and does not penetrate the underlying luminal tissue. As drawn together by suture 66 across the central portion of stent 10, lumen 68 of the testicular end is accurately approximated against lumen 70 of the urethal end 54 with a superior mucosa-to-mucosa and muscle-to-muscle alignment between the testicular and urethal ends.

After the two ends of the vas are drawn together with single stitch 66, the forceps are removed and the vas is pushed through incision 58 and back into the scrotum. A single suture is placed to close incision 58. Ultimately, the stent is absorbed, leaving an open lumen providing a continuous, unobstructed passage between the limbs of the reunited vas.

Some changes may be made in the structure of the stent disclosed herein without departing from the principles of the present invention. Stent 10 for example, has portions of greater and lesser cross-sectional dimensions to accommodate differences in the luminal diameters encountered after resectioning of small tubular organ structures. If a stent is to be used to provide internal support during healing of a larger diameter tubular organ structure however, or if the organ structure has not been subjected to resectioning, a somewhat different structure such as that of stent 80 shown in FIG. 8 may be more desirable. Stent 80, having only a single elongate portion 12, is characterized by the substantial uniformity in its cross-sectional dimensions. Stent 80 is formed with a plurality of axially spaced apart annular ribs 20 having rounded exterior surfaces, disposed around the exterior surface of portion 12. Two of these ribs form the rounded terminal end elements of the stent. The rounded exterior surfaces of ribs 20 and the disposition of two of those ribs to form the terminal elements of stent 80 assure that the exterior surface of the stent is free of sharp angles and edges. Central canal 24 extends along the axial length of stent 80 and opens through the distal extremities of the stent. The interior diameter of canal 24 is substantially constant throughout the length of stent 80.

Stent 80 is formed from a tissue absorbable material such as Dexon and is quite flexible. After stent 80 has been inserted within the lumen of a tubular organ structure and both end sections of the organ structure have been drawn together over the exterior of stent 80, the stent is left in place and ultimately absorbed. During healing of the anastomose, stent 80 provides a continuous, unobstructed passage through the lumen.

FIG. 9 shows a greatly enlarged view of a stent 90 for use in anastomosis of the smaller tubular organ structures such as the ureter, urethra or similar sized ducts. Stent 90 includes a first elongate element 12' having a greater cross-sectional dimension, a rounded central element 15' and a second elongate element 14' having a lesser cross-sectional dimension than element 12'. A plurality of annular ribs 20, 22 of different exterior diameters and having rounded exterior surfaces are respectively disposed axially spaced apart around the exterior circumferential surfaces of first elongate element 12' and second elongate element 14'.

A protruding member 92 extends axially outward from one end of each of first element 12' and second element 14'. The protruding members have a short, cylindrical neck portion 94 joined on one side to the body proper of elements 12', 14' and surmounted on the other side by the base of a flange 96 having a truncated conical shape. A central canal 24 extends along the axial length of stent 90, through first and second elements 12', 14', and neck portions 94, opening at the distal extremeties of elements 12', 14' and flanges 96. Although the exterior cross-sectional dimensions of the first and second elements of stent 80 and their associated annular ribs 20, 22 are different with element 12' and ribs 20 having greater exterior cross-sectional dimensions than element 14' and ribs 22, the interior diameter of canal 24 is substantially constant throughout both elements and their protruding members 92.

Central element 15' is shown in FIG. 9 with a generally oblong traverse-sectional shape and in FIG. 10 with a cylindrical cross-sectional shape. Opposite base ends of central element 15' are perforated by axially aligned orifices 98 having generally conical shapes with the exterior-sectional dimensions being greater than the interior dimensions. Orifices 98 provide access to a central cavity 24'. Stent 90 is formed from a tissue absorbable material such as Dexon and is quite flexible. The length and cross-sectional dimensions of stent 90 are determined primarily by the ranges of the interior diameters of the particular anatomical tubular organ structure to be recanalized. Each of the elongate sections 12', 14' may be manufactured in a wide variety of sizes while central element 15' may be made in a lesser number of sizes. All of these different sized elongate and central elements however, should share common dimensions in their protruding members 92 and orifices 98. The flexible characteristics of the materials from which these elements are made will then allow stent 90 to be assembled from elongate elements of selected, albeit different, sizes which can then be joined together simply by gently forcing the flange and neck of each protruding member through orifices 98 on opposite sides of central member 15. Once inserted, the base, or underside, surface of each flange 96 will rest against the inside surface of cavity 24 surrounding the inner dimension of orifice 98, thereby retentively positioning elongate elements 12', 14' on opposite sides of element 15' with central canals 24 of each element in axial alignment. When so assembled, stent 90 is available for implantation during anastomosis of a tubular organ structure.

FIG. 11 shows an alternative embodiment of a central element 15". Central element 15" incorporates three orifices 98 suitable for accommodating protruding members 92 such as those shown in FIG. 9. The arrangement of these three orifices allows two elongate elements of the same or different sizes to be assembled together with their central canals 24 either in axial alignment or in perpendicular alignment along any two of the three orifices 98. Alternatively, one orifice 98 may be closed by a plug 100 having a flange 96 and neck 102 suitable for insertion into and through orifice 98. While the base surface of flange 96 will retentively engage the inside surface adjoining orifice 98, thereby closing orifice 98 while assuring that plug 100 cannot be inadvertently removed from the orifice, the outer or greatest cross-sectional dimension of neck 102 should be sufficiently large to prevent the plug from being forced entirely into cavity 24'. The shank 104 of plug 100 may contain a hole 106 for purposes such as engaging the plug to facilitate its removal. It may be noted that one of orifices 98 in central element 15' can accommodate a drain line (not shown) made of a surgical grade of plastic tubing inserted either directly or via a collar having a flange neck receivable through one of the orifices. Such a drain line would allow bodily fluids such as urine or other liquids to be diverted during healing of an anastomose at a downstream location. Also, the third orifice allows assembly of a three-element key "TEE" for the administration of medication. The use of two plugs in conjunction with central element 15" can create a temporary or permanent blockage during certain surgical procedures.

It is apparent that the stent and the procedure described in the foregoing paragraphs advantageously minimize the amount of time required for anastomosis of an anatomical tubular organ structure. In the vasovasotomy described in the illustrative example, the total surgical time should be approximately ten minutes or less to connect one vas deferens. This diminution of surgical time provides a concomitant reduction in cost for the patient. The stent has no rough edges which might cause irritation of the organ tissue or provide a site for infection. The rounded ribs and rounded end elements minimize traumatization of the lumen and its muscular wall while the reduction of surgical damage such as perforations through the lumen avoids both unnecessary trauma to the organ structure and the formation of additional sites for postoperative infection. Moreover, the presence of the stent within the reunited lumen provides structural support during healing while the tissue absorbency of the stent assures that the exterior cavity incision can be closed at the conclusion of the anastomosis, thereby reducing both the time for patient recovery and the risk of infection of the tubular organ structure via the incision. The open, central canal of the stent allows effluent passage, thereby eliminating back pressure and the possiblity of effluent leakage at the site of the reunion. The adaptability of this procedure to open surgery eliminates a need for special microsurgical skill, thereby permitting an anastomosis to be performed by a greater portion of the medical community.

I claim:

1. A stent for surgical anastomosis of anatomical tubular organ structures, comprising:

tubular means made of a tissue absorbable material, having first portion of greater exterior cross-sectional dimension and a second portion of lesser exterior cross-sectional dimension, said first and second portions terminating in rounded elements, for coupling anatomical tubular organ structures having lumena of different internal diameters; and said tubular means containing a central canal having a substantially constant interior cross-sectional dimension between and through said rounded elements, extending through said first and second portions and said rounded elements.

2. The stent of claim 1, wherein said tubular means is made as a single, unitary device.

3. The stent of claim 1, wherein said tubular means includes a plurality of annular ribs spaced axially apart between said rounded elements and circumferentially surrounding the exterior of said first and second portions.

4. The stent of claim 3, wherein said ribs have greater cross-sectional dimensions than the respective underlying first and second portions.

5. The stent of claim 4, wherein the exterior surfaces of said annular ribs are rounded.

6. The stent of claim 3, wherein said tubular means is constructed as a single unitary device.

7. The stent of claim 1, wherein each of said end elements has a rounded exterior surface with exterior cross-sectional dimensions decreasing along an axial direction proceeding from the center of the stent.

8. The stent of claim 7, wherein the greatest cross-sectional dimension of each of said rounded elements is greater than the cross-section dimension of the respective adjoining first and second portions.

9. The stent of claim 1, wherein said first and second portions are formed of discrete elements each having a protruding member at one end, said tubular means includes a central element separate from said discrete elements with orifice means for retentively receiving said protruding members, and said central canal extends through said first and second elements, said protruding members and said central element.

10. The stent of claim 9, wherein said orifice means are disposed on opposite axial sides of said central element to assure axial alignment of said central canal through said first and second portions after joinder of said first and second portions to said central element.

11. The stent of claim 10, wherein said protruding elements each have a neck portion surmounted by a flange having a cross-sectional dimension greater than the cross-sectional dimension of said neck portion.

12. A stent for surgical anastomosis of anatomical tubular organ structures, comprising:

a tubular member made of a tissue absorbable material having an elongate first portion of greater exterior cross-sectional diameter and an elongate section portion of lesser exterior cross-sectional dimension, said portions terminating in terminal elements;

said terminal elements having rounded exterior surfaces; and said tubular member containing a central canal having a substantially constant cross-sectional dimension between said rounded elements, extending through said first and second portions and said terminal elements.

13. The stent of claim 12, wherein said tubular member is constructed as a single unitary device.

14. The stent of claim 12, wherein said tubular member includes an intermediate region providing transition between the cross-sectional dimensions of said first and second portions.

15. The stent of claim 12, wherein said first and second portions have a plurality of axially spaced apart annular ribs circumferentially surrounding the exterior surfaces of said first and second portions disposed between said terminal elements, and said ribs have greater cross-sectional dimensions than the respective underlying first and second portions.

16. The stent of claim 15, wherein the exterior surfaces of said first and second portions, said terminal elements and said annular ribs are free of sharp angles and edges, and each of said terminal elements has a rounded exterior surface with cross-sectional dimensions decreasing along an axial direction proceeding from said annular ribs.

17. The stent of claim 16, wherein the greatest cross-sectional dimension of each of said terminal elements is greater than the cross-sectional dimension of the respective adjoining first and second portions.

18. The stent of claim 12, wherein said first and second portions are formed of discrete elements each having a protruding member at one end, said tubular means includes a central element separate from said discrete elements with orifice means for receiving and retaining said protruding members, and said central canal extends through said first and second elements, said protruding members and said central elements.

19. The stent of claim 18, wherein said orifice means are disposed on opposite axial sides of said central element to assure axial alignment of said central canal through said first and second portions after joinder of said first and second portions to said central element.

20. The stent of claim 19, wherein said protruding elements each have a neck portion surmounted by a flange having a cross-sectional dimension greater than the cross-sectional dimension of said neck portion.

21. A stent for surgical anastomosis of anatomical tubular organ structures, comprising:

a tubular member made of material adsorbable by anatomical tissue, and having an intermediate portion joining a first portion of greater cross-sectional dimension and a second portion of lesser cross-sectional dimension, the distal ends of said first and second portions terminating in terminal elements, said member containing a central canal having a substantially constant cross-sectional dimension extending through said first and second portions;

said first and second portions having a plurality of axially spaced apart annular ribs circumferentially surrounding the exterior surfaces of said first and second portions disposed between said terminal regions;

said ribs having greater cross-sectional dimensions than the respective underlying first and second portions;

the cross-sectional dimension of each of said terminal elements being greater than the cross-sectional dimensions of the respective adjoining first and second portions; and the exterior surfaces of said annular ribs and terminal elements being free of sharp angles and edges.

22. The stent of claim 21, wherein said tubular member and said annular ribs are made as a unitary structure.

23. A stent for surgical anastomosis of anatomical tubular organ structures, comprising a tubular member made of material absorbable by tissues of the anatomical organ structures and having first and second elongate portions providing underlying exterior surfaces of different and lesser cross-sectional dimensions, a plurality of annular elements axially spaced apart and circumferentially surrounding said underlying exterior surfaces, said annular elements having greater cross-sectional dimensions than respective ones of said first and second elongate portions of said tubular member; a pair of said annular elements forming terminal portions at opposite ends of said tubular member, and a central canal extending through and opening at said opposite ends of said tubular member, said central canal having a substantially uniform interior cross-sectional dimension.

24. A stent for surgical anastomosis of anatomical tubular organ structures, comprising:
a tubular member made of a tissue absorbable material and having an elongate first portion of greater cross-sectional diameter and an elongate second portion of lesser cross-sectional dimension, said portions terminating in terminal elements;
said terminal elements having rounded exterior surfaces; and
said tubular member containing a central canal extending through said first and second portions;
said first and second portions being discrete elements each having a protruding member at one end;
said tubular means including a central element separate from said discrete elements and having orifice means for receiving and retaining said protruding members; and
said central canal being of substantially uniform cross-sectional dimension, extending through said first and second discrete elements, and extending through said protruding members and said central elements.

25. The stent of claim 24, wherein said orifice means are disposed on opposite axial sides of said central element to assure axial alignment of said central canal through said first and second portions after joinder of said first and second portions to said central element.

26. The stent of claim 25, wherein said protruding elements each have a neck portion surmounted by a flange having a cross-sectional dimension greater than the cross-sectional dimension of said neck portion.

27. The stent of claim 24, further comprised of deformable means disposed at the distal end portions of said protruding members for cooperating with cross-sectional configurations of said orifice means to restrain said protruding members from disengaging said intermediate portion.

* * * * *